United States Patent [19]

Zemel

[11] Patent Number: 4,551,425
[45] Date of Patent: Nov. 5, 1985

[54] PYROELECTRIC GAS SENSOR

[75] Inventor: Jay N. Zemel, Jenkintown, Pa.

[73] Assignee: Trustees of the University of Pennsylvania, Philadelphia, Pa.

[21] Appl. No.: 425,400

[22] Filed: Sep. 28, 1982

[51] Int. Cl.$^4$ .................... C12Q 1/00; G01N 25/32; G01N 25/48
[52] U.S. Cl. .......................................... 435/4; 374/45; 422/69; 422/88; 422/90; 422/95; 435/288; 435/291; 435/807; 436/147; 436/151; 436/152
[58] Field of Search .................... 436/147, 151, 152; 422/69, 88, 90, 94–98; 435/4, 288, 291, 807; 73/27 R, 26; 374/45

[56] References Cited

U.S. PATENT DOCUMENTS

| | | | |
|---|---|---|---|
| 3,467,501 | 9/1969 | Groszek | 73/27 R |
| 3,519,924 | 7/1970 | Burton | 73/204 X |
| 3,861,879 | 1/1975 | Taylor | 422/98 X |
| 4,021,307 | 5/1977 | Mosbach | 435/12 |
| 4,045,178 | 8/1977 | Okinaka et al. | 422/98 |
| 4,332,157 | 6/1982 | Zemel et al. | 73/26 |

FOREIGN PATENT DOCUMENTS 0021696 7/1981 European Pat. Off. .
56-32606 4/1981 Japan .

OTHER PUBLICATIONS

Zemel et al., "Sensors and Actuators", 1, (1981), 427–473.

Primary Examiner—Arnold Turk
Attorney, Agent, or Firm—Stevens, Davis, Miller & Mosher

[57] ABSTRACT

A pyroelectric substrate is provided with a heater and at least one set of electrodes for sensing charge redistributions due to changes in the substrate temperature. In a preferred embodiment, there are two interdigitated electrodes, one coated with an absorber/desorber material. The heater pulsatingly raises the temperature of the substrate past the desorption temperature of a fluid of interest. If the fluid was exposed to the absorber/desorber material prior to heating, a portion of the fluid will have been absorbed. When the substrate reaches the desorption temperature, additional heat pulses will not increase the substrate temperature significantly until the fluid has desorbed. Thus, heat used in changing state does not raise the substrate temperature and, lacking a temperature change, reduces the charge redistribution sensed by the electrode coated with the material. Its output is compared with the uncoated electrode (whose temperature continues to rise) and the difference is equal to the amount of fluid desorbed and the temperature is indicative of the species of fluid desorbed.

20 Claims, 15 Drawing Figures

PYROELECTRIC GAS SENSOR

BACKGROUND OF THE INVENTION

The present invention relates generally to solid state gas sensing devices and specifically to a gas sensor using pyroelectric effects.

In conjunction with studies related to high power sources of microwave and millimeter wave radiation, attention has focused on problems in the vacuum tube technology for generating this radiation. Specifically, the cathodes of such vacuum tube devices are sensitive to contamination by residual gases in the tube as well as out-gassing products from tube components as they heat up during operation. In view of the processing of these vacuum tubes (heating to temperatures in the vicinity of 450° C.) rather stringent environmental parameters are placed on any sensor utilized to measure internal contaminants.

Pyroelectric substances are a class of substances which exhibit an induced surface charge when the temperature of the material changes. If a pyroelectric substrate is polarized at a temperature above its Curie temperature, and electrodes are placed on either side of the substrate (across the poling direction) a charge will be developed across the electrodes when the temperature of the substrate is changed. The amount of voltage and/or current will be proportional to the rate of change of temperature.

An article appearing in *Sensors and Actuators*, Vol. 1, 1981, entitled "Non-FET Chemical Sensors", by Zemel, Keramati, Spivak and D'Amico examines the possibility of utilizing pyroelectric substrates as a gas sensor, and is herein incorporated by reference. The article discusses the anticipated signal from a pyroelectric substrate which is being heated over a period of time. A similar graph of signal output versus time is shown in FIG. 1. The solid line indicates that as heat is applied, the temperature of the substrate changes and this change in temperature provides an output signal from the electrodes on the substrate.

However, if a material is placed on the substrate and begins to undergo a phase change at time $T_1$ the graph of signal versus time would be as shown in dotted lines. Although the heat input to the substrate is the same as the solid line graph, the heat required to change the state of the material on the substrate would prevent an increase in substrate temperature for some short period of time (until all the material has undergone phase change). Because the temperature of the substrate is not changing at this time $T_1$, the signal will not increase normally and, in some instances, may actually decrease. This is analogous to the high school experiment in which a Bunsen burner is used to boil water in a thin plastic cup. The cup's temperature rises to that of boiling water and is maintained constant at that temperature until all of the water is boiled away at which time, of course, the cup is heated beyond the temperature of boiling water to its melting point and/or combustion point. However, while the water is boiling away, the temperature of the cup remains at a relatively steady temperature. In our pyroelectric substance, because the substrate is maintained at a relatively constant temperature while the material on its surface is changing phase, the signal output of the pyroelectric substrate is greatly diminished.

Also disclosed in the article is the experimental response of a pyroelectric sensor to the melting of 8 mg of In-Sn solder located on the substrate suggesting that indeed such a pyroelectric sensor was possible. However, theoretical predictions do not necessarily take into account practical realities. It is desirable to be able to differentiate between two or more materials on the substrate surface and thus extremely small substrate temperature increments are desired in order to see the effect of each of two or more materials as they separately absorb heat from the substrate during their melting and/or vaporization. Further, the noise level of a single sensor clouds the sensitivity of the device such that it is difficult to know whether the output is an indication of a material on the substrate, or a random noise signal which has been acquired. Thus, selectivity and sensitivity are problems associated with the experimental pyroelectric gas sensor.

Also known is the use of a pyroelectric substrate as a gas dosimeter as disclosed in U.S. Pat. No. 3,861,879 to Taylor, issued Jan. 21, 1975. Here the exothermic oxidation of carbon monoxide in the presence of a suitable catalyst causes a temperature change in the pyroelectric with a resulting charge redistribution which is sensed.

SUMMARY OF THE INVENTION

In accordance with the above disadvantages, it is an object of the present invention to provide a sensor capable of indicating the presence, concentration and identity of a fluid (gas or liquid) in a test medium (gas or liquid).

It is a further object of the present invention to utilize a pyroelectric substrate as a sensor of a fluid in a test medium.

The above and other objects are achieved in accordance with the present invention by providing a polarized pyroelectric substrate with sensor electrodes sandwiching the substrate in the polarized direction. The substrate is also provided with a heater element which applies a fluctuating heat input to the substrate. The constantly changing temperature of the substrate provides a periodic output from the sensor electrodes. In a preferred embodiment, two electrodes with substantially the same physical characteristics are operated together with only one electrode having a material capable of absorbing the fluid whose existence is to be determined. The outputs of the two electrodes are provided to a differential amplifier which provides an output indicative only of the difference between the signals produced by the two substrates. The fluctuating heat input gradually raises the temperature of the substrate cycle by cycle through the desorption temperature (that temperature at which the tested-for fluid melts, vaporizes, or sublimates). If an output is present at the differential amplifier then a fluid has desorbed from the material on the pyroelectric substrate. The extent of the output of the differential amplifier is an indication of the concentration of the desorbing fluid and the temperature at which desorption begins is an indication of the species or identity of the fluid.

A further embodiment of the invention utilizes a lock-in amplifier driven at the same frequency as the pulsing heater input to the substrates which serves to amplify only the differential output which is directly resultant from the fluctuating heat input.

A further embodiment utilizes a fluctuating fluid concentration supplied to the pyroelectric substrate with the substrate heated in a gradual manner. When the substrate temperature reaches the point at which desorption occurs during a pulse of low concentration and adsorption occurs during a pulse of high concentration, a large differential output will occur. This temperature is similarly indicative of the species of fluid while the magnitude of the differential signal is indicative of the concentration of the fluid. This pulsed-gas embodiment can also be advantageously combined with a lock-in-amplifier tied to the gas pulsation frequency.

BRIEF DESCRIPTION OF THE DRAWINGS

A more complete appreciation of the invention, and many of the attendant advantages thereof will be readily apparent by reference to the accompanying drawings, wherein:

FIGS. 2a, 2b and 2c are top, bottom and side views, respectively, of a pyroelectric gas sensor in accordance with the present invention;

DETAILED DESCRIPTION OF PREFERRED EMBODIMENTS

Figure 1:
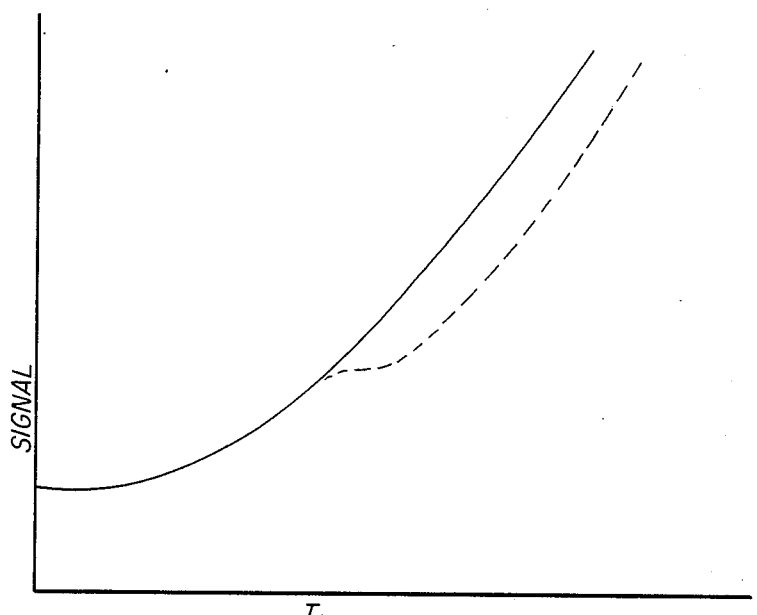
FIG. 1 is a graph of pyroelectric substrate signal versus time for a substrate with and without a fluid present thereon.
Figure 2C:
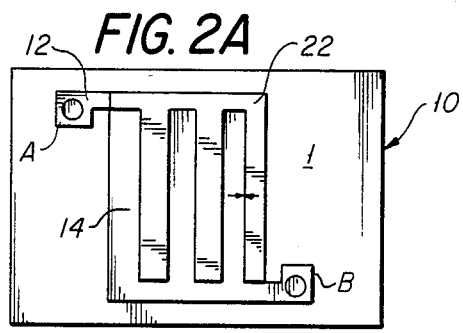
Figure 2C:
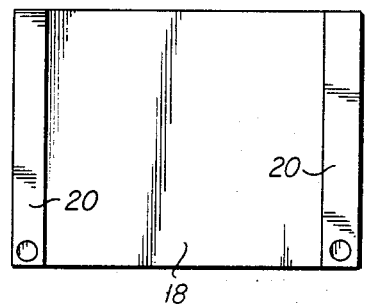
Figure 2C:
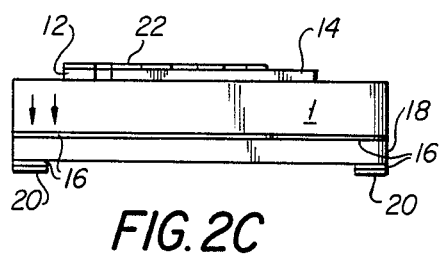

Referring now more particularly to the drawings, wherein like numerals represent like elements throughout the several views, FIGS. 2a, 2b and 2c illustrate one embodiment of the pyroelectric gas sensor 10. Although other materials could be used, lithium tantalate LiTaO$_3$ was chosen because of its high Curie temperature (618° C.). A z cut crystal of LiTaO$_3$ measuring 1.2×1.4×0.03 cm was prepared in the following manner. The LiTaO$_3$ wafer was first cleaned in trichloroethylene followed by acetone, alcohol and distilled water. The surface was then treated with cold HNO$_3$/H$_2$SO$_4$ solution to remove any metallic impurities followed by distilled water and ethyl alcohol. The wafer was then blown dry with pure N$_2$.

A 3000 Å thick Au film was deposited on the substrate. A positive A-J 1350 photoresist was spin coated on the wafer and subjected to the photoprocessing to provide the interdigitated electrode means A and B with a 50μ space separating adjacent fingers (the distance shown by the opposing arrows in FIG. 2a). After removal of the excess gold film by an aqua regia etch, the photoresist is then removed with acetone followed by an ethyl alcohol rinse and drying by means of nitrogen gas. The remaining interdigitated gold structure is shown in FIG. 2a as elements 12 and 14 associated with electrodes A and B, respectively. On the back side of the wafer (shown in FIG. 2b) an overall layer 100 Å of Cr 16 is deposited after which a layer of 3000 Å thickness of NiCr 18 is deposited to form the heater resistor 18. An additional 100 Å of Cr is deposited through a mask with a further 3000 Å Au 20 to form the heater contact pads. The resulting resistor has a resistance on the order of 2 to 4 ohms.

As can be seen in FIG. 2c, the electrode contacts A and B are located on a plane normal to the polarization direction of the wafer (polarization direction indicated by the arrows in FIG. 2c). An activated charcoal film is provided on electrode A as shown in FIGS. 2a and 2c. Different materials could be substituted for the charcoal 22 in order to change the response of the pyroelectric gas sensor to different gases and/or liquids. The two interdigitated electrodes act as charge sensors for the pyroelectric structure and have the same total area. The interdigitating of the electrodes is to minimize the effect of any temperature inhomogeneities due to geometry or material properties of the thin film heater. As the substrate is heated, a current is generated at each electrode. Assuming that the heat loss at each electrode is the same, a differential signal at the two electrodes ought to be zero subject to the proviso that the area, emissivity, and gas desorption is the same for each electrode.

Figure 3:
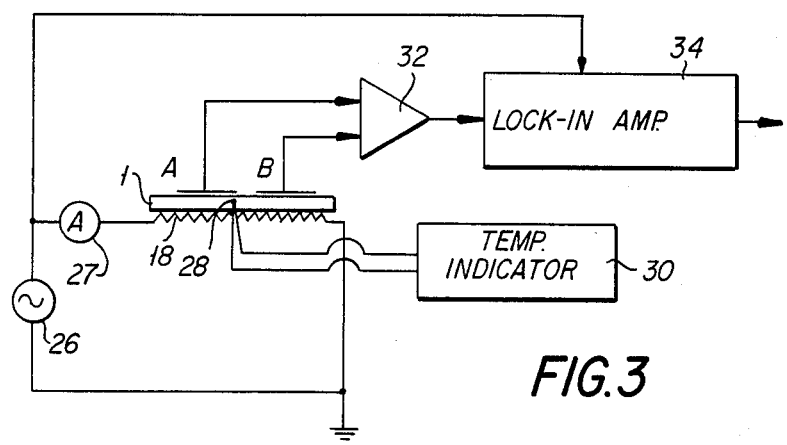
FIG. 3 is an electronic block diagram illustrating the connections and electronic processing of one embodiment of the present invention.

FIG. 3 illustrates the electronic interconnections for utilizing information provided by the pyroelectric gas sensor. The pyroelectric substrate 1 has the electrical resistance heater 18 mounted on the bottom thereof which, together with ammeter 24 and power supply 26 comprise the means for varying the temperature of the pyroelectric substrate.

A thermocouple 28 and temperature indicator 30 comprise a means for measuring and indicating the temperature of the absorbing/desorbing charcoal. A differential amplifier 32 provides an output indicative of the difference between signals produced by electrodes A and B. In a preferred embodiment, a lock-in amplifier 34 serves to amplify only input signals which are correlated with the heating means in this embodiment. In one embodiment, the power input to the resistance heater will be a series of pulses having a given frequency, and as can be seen from FIGS. 4a, 4b and 4c, the output of each individual electrode will be in a direct phase relationship with fluctuations in the substrate temperature caused by the pulsating heat input of the power supply. The lock-in amplifier serves as a notch filter for the frequency or subharmonic thereof of power supply 26.

Figure 4A:
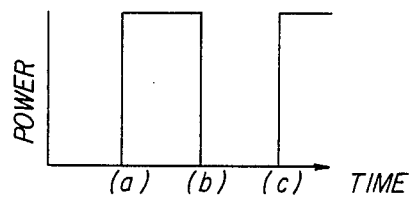
FIGS. 4a, 4b, and 4c illustrate power applied to the substrate, substrate temperature, and current generated at the substrate electrodes, respectively, for the embodiment shown in FIG. 3.
Figure 4B:
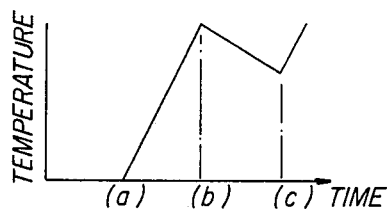
Figure 4C:
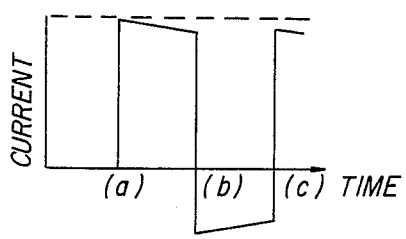

Turning to FIGS. 4a–4c, a better understanding of one embodiment of the present invention may be had. As previously noted, power is applied to the resistance heater 18 in a pulse-type fashion being on from time (a) until time (b) and then off from time (b) until time (c). In this embodiment, the on/off time durations are equal although they need not be. When heat is supplied to the pyroelectric substrate, its temperature will rise as indicated in FIG. 4b between times (a) and (b) and by virtue of conduction and radiation losses, the temperature of the substrate will drop when power is not applied to it as is shown between time periods (b) and (c). It will be recalled that a pyroelectric substrate only produces an output when the temperature of the substrate is changing, i.e., when dT/dt is not equal to zero. Additionally, because the heat lost (at least initially) between times (b) and (c) is less than the heat gained between times (a) and (b), the temperature of the substrate will gradually rise.

However, because the conductive, convective and radiation losses of heat are greater at higher temperatures, the amount of temperature change for each additional heat pulse will be less as higher temperatures are reached. Because the temperature increase between pulses becomes less and less as the substrate warms up, the current or signal developed at the electrodes by the pyroelectric substrate will be of less magnitude as time goes on. This is illustrated as the difference in current magnitude in FIG. 4c at time (a) as compared with time (c). It can also be observed by referring to FIG. 4c that the temperature change of the substrate is less during the cooling cycle than in the heating cycle as the negative going polarity has a much lower amplitude than the positive going polarity.

Figure 5A:
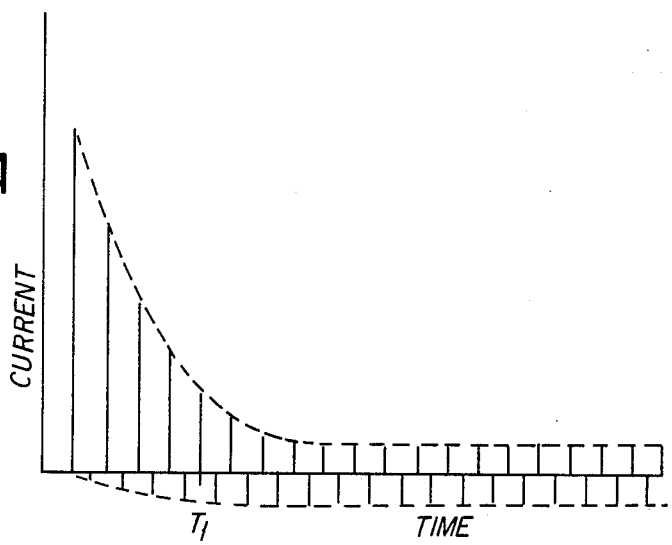
FIGS. 5a and 5b illustrate current versus time for the embodiment of FIG. 3 without and with the test fluid present, respectively.
Figure 5B:
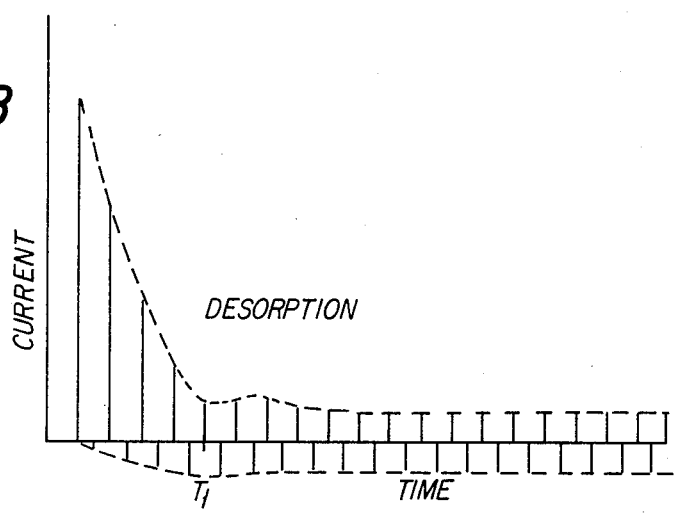

FIG. 5a illustrates current produced by one electrode over a substantial period of time in much the same manner as did FIG. 4c. It can be seen that after a period of time, a temperature will be reached at which the heat added during the power supply pulse is equal to the heat lost due to conduction, convection and radiation between pulses. Therefore, it would be possible to compute the current generated at a given electrode on the basis of the input heat, the convection, conduction and radiation losses expected from the substrate, and the thermal constant of the substrate, whether or not the substrate included an absorber/desorber material such as charcoal as previously noted. However, where there is a material absorbed into the absorber/desorber material, if its desorption temperature is within the operating range of the pyroelectric gas sensor, i.e., less than the maximum temperature reached by the substrate, then additional heat will be taken away from the substrate by this evaporation process. Because a greater than normal amount of heat will be taken away especially between pulses, the negative going current produced at the electrode will increase to a greater level than that shown in FIG. 5a. Furthermore, because the thermal energy is utilized to a certain extent in boiling off the fluid from the absorber/desorber, the temperature of the substrate will not increase as much per power pulse and thus the current generated at the electrode will be less in FIG. 5b than in FIG. 5a (compare current levels at time $T_1$). Thus, a single electrode can produce an indication of a fluid desorbing from the absorber/desorber material based on a comparison with the same electrodes current versus time profile without the fluid present. Additionally, the temperature at which the fluid desorbs (determined from the known temperature/time curve of FIG. 4b) will provide an indication of the species or type of material desorbing. For the purpose of this specification, fluid is defined as any unknown material for which the pyroelectric gas sensor is designed and could be a gas or liquid. Similarly, a test medium is defined as a gas or liquid medium in which the fluid is suspended and carried past the pyroelectric gas sensor.

Figure 8:
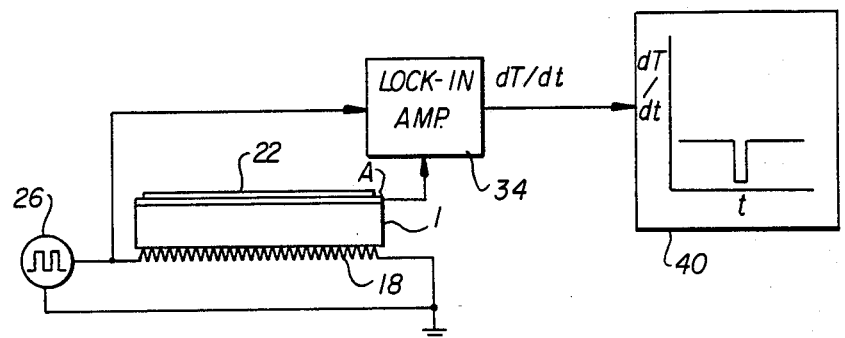
FIG. 8 is an electronic block diagram of a further embodiment of the present invention.

Such a single electrode pyroelectric gas sensor is illustrated in FIG. 8.

The power supply 26 provides a pulsating current to resistance heater 18 on pyroelectric substrate 1. If the absorber/desorber material 22 located on electrode A has absorbed a fluid of interest, this fluid will have a characteristic temperature of desorption. As the substrate is heated and approaches the desorption temperature, the rate of change of substrate temperature (dT/dt) should be relatively constant although it might decrease to a greater extent at higher temperatures due to an increasing radiative loss component. The output of the lock-in amplifier 34 will reflect this relatively constant temperature change of the substrate with a relatively constant output. However, when the desorption temperature of the fluid on material 22 is reached, a portion of the heat generated by the resistance heater 18 will be utilized in vaporizing the fluid with the result that the rise in temperature of the substrate will be substantially less. Because the substrate temperature rise is less, the change in temperature per unit time (dT/dt) will drop as shown in the graph contained by output indicator 40. The actual temperature of the substrate when the drop in dT/dt occurs can be computed based on the time at which the change occurs times the average change per unit time. Thus, the presence of a fluid in the material 22 and its temperature of desorption is indicated on indicator 40. Such an indicator could be a cathode ray tube, an X-Y plotter, a digital printout, etc. The amount of fluid which desorbs from material 22 is indicated by the amount of time necessary to desorb the material once the desorption temperature is reached, i.e., the width of the gap in dT/dt on indicator 40. Again, utilization of phase lock amplifier 34 or other correlation equipment, while not critical, affords better signal acquisition and noise rejection.

Figure 9:
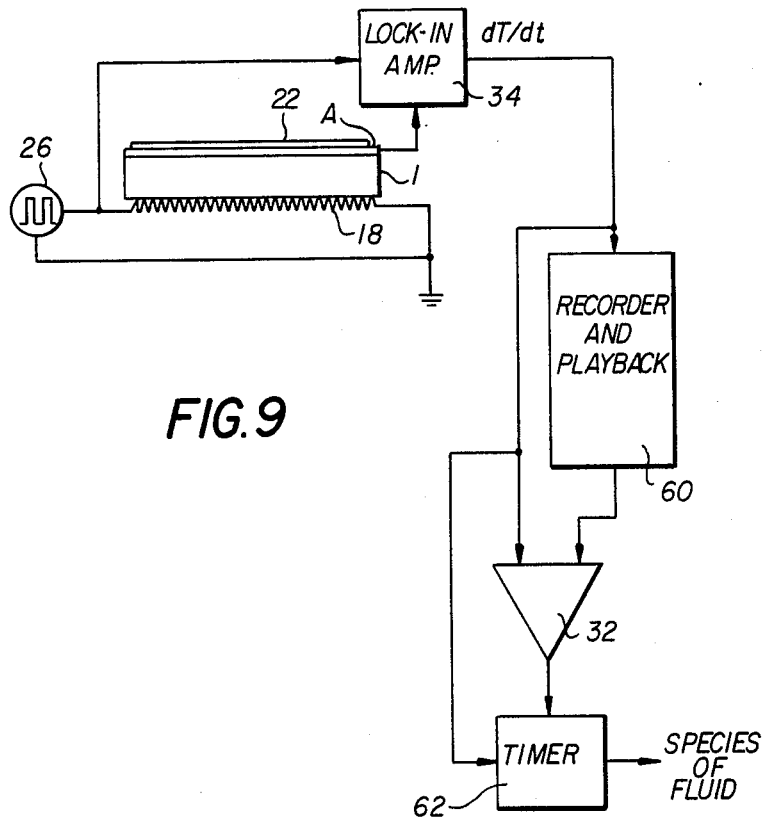
FIG. 9 is an electronic block diagram of a further embodiment of the present invention.

It is also possible to utilize the device shown in FIG. 8 without the output indicator 40 as in FIG. 9 by comparing dT/dt with the material 22 exposed to the unknown fluid with the dT/dt curve of the substrate without the unknown fluid present. This requires recording in recorder 60 at least one curve and then comparing the recorded curve with the opposite dT/dt output live (if the dT/dt for the unknown fluid is recorded, then the dT/dt for the substrate without the unknown fluid is live and vice versa) and looking for differences between the two signals. The time from timer 62 at which a significant difference occurs is indicative of the species of fluid desorbed from material 22 as the time of desorption can be related to the temperature of desorption which is characteristic of different fluids.

Figure 6:
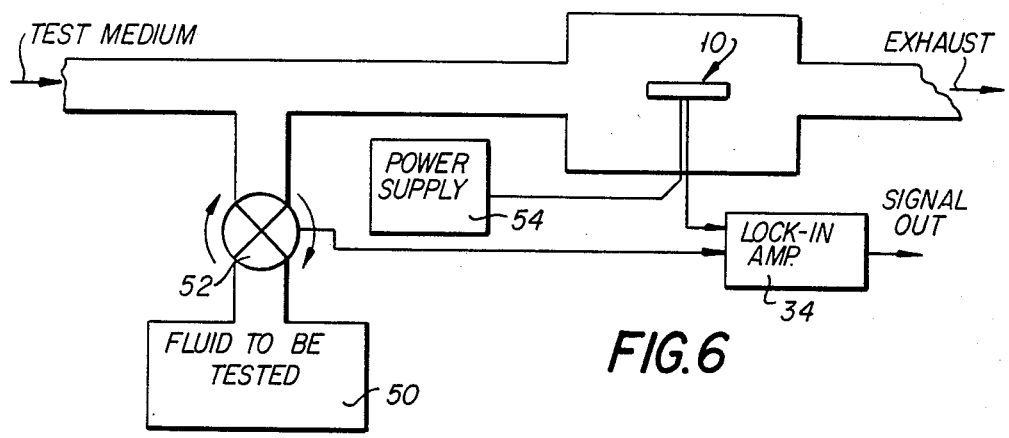
FIG. 6 is a further embodiment of the present invention where the fluid concentration is periodically varied.
Figure 7A:
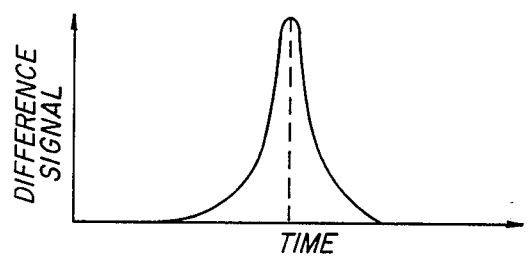
FIGS. 7a and 7b illustrate the difference signal output versus time and the substrate temperature versus time, respectively, for the pyroelectric gas sensor shown in FIG. 6.
Figure 7B:
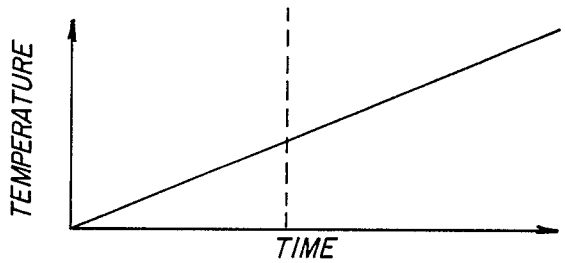

A further embodiment of the pyroelectric gas sensor utilizes pulsations in gas concentration to vary the absorption/desorption on the material 22 and thus affect the rate of change of temperature of the pyroelectric substrate. Such an embodiment is illustrated in FIG. 6 in which a supply of the fluid to be tested 50 is pulsatingly added to the test medium by means of a rotating or pulsating valve 52. Thus, a periodically increasing/decreasing concentration of the fluid to be tested passes over the pyroelectric gas sensor 10 before the gas is exhausted. Although power supply 54 could provide a pulsating periodic output as in FIG. 4a or a sine wave output, in a preferred embodiment the power supply provides power to the resistance heater such that the temperature of the substrate increases linearly with respect to time, as shown in FIG. 7b.

Although a single element sensor would work, a dual element sensor with a differential amplifier (such as that shown in FIG. 3) is believed to be a preferred embodiment. The differential amplifier and the individual elements are included in the pyroelectric gas sensor 10 shown in FIG. 6. The fluctuating fluid (gas or liquid) will absorb on the absorber/desorber material of the pyroelectric gas sensor and at low temperatures this surface will become saturated. As the gas pulsates in concentration, the saturated absorber/desorber material will be relatively unaffected and there will be no heat exchange due to absorption/desorption. Similarly, at very high temperatures, there is no substantial amount of gas absorbed on the absorber/desorber material surface because the mean residence time is so small due to molecular activity (regardless of the gas concentration).

However, at some intermediate temperature, the absorber/desorber material will absorb fluid in the high concentration regime and desorb fluid during the low concentration regime. A consequence of this gas exchange is that heat is removed on desorption and added on absorption. Because there is a heat exchange, there will be a change in dT/dt and there will be a difference in the signal outputs of the electrode contacts of the pyroelectric gas sensor. The differential amplifier will provide the difference output and because this output will vary at a function of the gas pulsation frequency (although not necessarily at the same phase) the lock-in amplifier passes only that narrow frequency band corresponding to the rotating valve frequency. When the temperature is reached which achieves a maximum change in substrate temperature per gas pulse cycle, a peak will be reached as indicated in FIG. 7a at the dotted line. This dotted line temperature will be a characteristic of the species of fluid and the amplitude of the difference signal at the maximum will be a characteristic of the concentration of the fluid to be tested. This peak of "resonance" can be a very dramatic indication and with an appropriate lock-in amplifier or other correlation measurement is capable of indicating the presence and concentration of extremely minute quantities of fluid in the test medium.

The pyroelectric gas sensor is described with regard to several examples. However, the concept of utilizing the absorption and/or desorption of a fluid onto a material to change the rate of change of temperature on a pyroelectric substrate can take many other forms, depending upon the specific requirements. The fluid to be tested could be a gas or liquid and the test medium could be a gas or liquid with the fluid dissolved therein. The test medium could easily be dispensed with or be considered a vacuum in either of the disclosed embodiments. The fluctuating power supply in the various embodiments could be a pulse, sine wave, or gradually increasing power. The pyroelectric gas sensor, particularly as discussed with reference to FIG. 3 could be exposed to the fluid to be tested and subsequently cycled through its temperature profile to determine the gas present. However, upon continuous exposure of the pyroelectric gas sensor to the fluid to be tested, a similar "resonance" would be encountered as the critical desorption temperature is reached for the particular fluid being tested. Because the temperature of the substrate fluctuates, it would tend to desorb a greater portion of the fluid at the higher temperatures and absorb more of the fluid at the lower temperatures. This periodic desorption and absorption would cause a much greater differential output from the gas sensor similar to that illustrated in FIG. 7a.

Although the temperature of the absorber/desorber material can readily be calculated, it may be useful to include a temperature measuring means as previously discussed with reference to FIG. 3. The size of the pyroelectric gas sensor can be made extremely small by currently available photolithographic techniques. This reduction in size not only increases the frequency response of the pyroelectric gas sensor, but also increases its sensitivity to fluids being tested. It has also been found that some materials may be more suitable for the absorber/desorber material if a particular fluid presence and/or concentration is to be detected.

One aspect of the pyroelectric gas sensor is the chemically sensitive layer. It is only necessary that it provide some temperature change as a consequence of the presence of the desired fluid in order for the sensor to provide an output indication thereof. Therefore, if a suitable enzyme or coenzyme is bonded to the surface of the pyroelectric (in the vicinity of one electrode in the dual or differential embodiment) it would be possible to detect the heat generated by the interaction of the bound enzyme or coenzyme with the corresponding coenzyme or enzyme, respectively. A catalytic material such as is disclosed in Taylor could also be used but with much greater accuracy as the sensor being driven with heat source provides a much more accurate indication of catalytic reactions on the pyroelectric substrate surface. In a catalytic embodiment, the reaction temperature like the previously discussed desorption temperature, would be an indication of the type of substance present in the fluid and the magnitude of the temperature shift (or difference in the differential measurement) would be an indication of the concentration of the substance present. It would also be possible to place the pyroelectric substrate directly on a field effect transistor as the gate such that charge redistributions caused by temperature changes in the pyroelectric substrate serve to control current flow through the transistor. Thus, an extremely small chemical sensor could be provided with a built in first stage amplifier.

In view of the above discussion, many modifications and applications of the pyroelectric gas sensor will be obvious to those of ordinary skill in the art. Therefore, the invention described herein is limited only by the appended claims.

The embodiments of the invention in which an exclusive property or privilege is claimed are defined as follows:

1. A pyroelectric fluid sensor for determining at least the presence of a fluid in a test medium, said sensor comprising:
    a pyroelectric substrate;
    first electrode means for deriving a signal from said pyroelectric substrate when the temperature of said substrate changes;
    means for fluctuating the temperature of said pyroelectric substrate during heating to a maximum temperature during sensing for the presence of said fluid in said test medium;
    temperature dependent means for absorbing and for desorbing said fluid, said absorbing/desorbing means in thermal contact with said substrate; and
    means for recording and comparing said signal when said absorbing/desorbing means is exposed to a fluid-free test medium with said signal when said absorbing/desorbing means is exposed to a test medium in which the presence of said fluid is to be determined and for indicating any difference in said signals.

2. The pyroelectric fluid sensor according to claim 1, wherein said comparing means includes means, responsive to the magnitude of any difference between said signal when said absorbing/desorbing means is exposed to a fluid-free test medium and said signal when said absorbing/desorbing medium is exposed to a test medium in which the presence of said fluid is to be determined, for indicating the concentration of said fluid in said test medium.

3. A pyroelectric fluid sensor for determining at least the presence of a fluid in a test medium, said sensor comprising a pyroelectric substrate, wherein
said pyroelectric substrate has at least first and second portions;
first electrode means for deriving a first signal from said first portion of said pyroelectric substrate when the temperature of said first portion changes;
second electrode means for deriving a second signal from said second portion of said pyroelectric substrate when the temperature of said second portion changes;
means for fluctuating the temperature of said first and said second portions of said pyroelectric substrate during heating to a maximum temperature;
temperature dependent means for absorbing and for desorbing said fluid, said absorbing/desorbing means in substantial thermal contact with only said first portion of said pyroelectric substrate; and
means for comparing said first and second signals and for indicating the presence of said fluid when said first signal is substantially different from said second signal.

4. The pyroelectric fluid sensor according to claim 3, wherein said comparing means includes means responsive to the magnitude of difference between said first and second signals, for indicating the concentration of said fluid in said test medium.

5. The pyroelectric fluid sensor according to claim 1, further including means, responsive to a difference between said signal when said absorbing/desorbing means is exposed to a fluid-free test medium and said signal when said absorbing/desorbing means is exposed to a test medium in which the presence of said fluid is to be determined, for measuring and indicating the temperature of said absorbing/desorbing means when said difference is detected, said temperature comprising an indication of species of said fluid.

6. The pyroelectric fluid sensor according to claim 3, further including means, responsive to a difference between said first and second signals, for measuring and indicating the temperature of said absorbing/desorbing means when said difference is detected, said temperature comprising an indication of species of said fluid.

7. The pyroelectric fluid sensor according to claim 2, further comprising means, responsive to a difference between said signal when said absorbing/desorbing means is exposed to a fluid-free test medium and said signal when said absorbing/desorbing means is exposed to a test medium in which the presence of said fluid is to be determined, for measuring and indicating the temperature of said absorbing/desorbing means when said difference is detected, said temperature comprising an indication of species of said fluid.

8. The pyroelectric fluid sensor according to claim 4, further including means, responsive to a difference between said first and second signals, for measuring and indicating the temperature of said absorbing/desorbing means when said difference is detected, said temperature comprising an indication of species of said fluid.

9. A pyroelectric fluid sensor for determining at least the presence of a fluid in a test medium, said sensor comprising:
a pyroelectric substrate;
electrode means for deriving a signal from said pyroelectric substrate when the temperature of said substrate changes;
means for fluctuating the temperature of said pyroelectric substrate during heating to a maximum temperature;
temperature dependent means for absorbing and desorbing said fluid, said absorbing/desorbing means in substantial thermal contact with said substrate; and
means, responsive to said signal, for indicating the rate of change of substrate temperature with time (dT/dt) where a change in the slope of dT/dt versus time is an indication of the presence of said fluid.

10. The pyroelectric fluid sensor according to claim 9, further including means, responsive to the existence of a change in the slope of dT/dt versus time, for measuring and indicating the temperature of said absorbing/desorbing means, said temperature comprising an indication of species of said fluid.

11. The pyroelectric fluid sensor according to claim 9, wherein said indicating means further includes means, responsive to the magnitude of change in the slope of dT/dt versus time, for indicating the concentration of said fluid in said test medium.

12. The pyroelectric fluid sensor according to claim 11, further including means responsive to a change in the slope of dT/dt versus time, for measuring and indicating the temperature of said absorbing/desorbing means, said temperature comprising an indication of species of said fluid.

13. The pyroelectric fluid sensor according to one of claims 1-8, wherein said temperature fluctuating means comprises a means for periodically varying the temperature at a given frequency, said comparing means further including lock-in amplifier means for amplifying signals correlatable with said given frequency.

14. A pyroelectric fluid sensor according to one of claims 9-12 wherein said temperature fluctuating means comprises a means for periodically varying the temperature of said substrate at a given frequency and said indicating means further includes correlation type amplifier means for amplifying signals correlatable with said given frequency.

15. A pyroelectric fluid sensor for determining at least the presence of a fluid in a test medium, said sensor comprising:
a pyroelectric substrate;
electrode means for deriving a signal from said pyroelectric substrate when the temperature of said substrate changes;
means for changing the temperature of said pyroelectric substrate;
temperature dependent means for absorbing and for desorbing said fluid, said absorbing/desorbing means in substantial thermal contact with said pyroelectric substrate;
means for applying said fluid in a periodically varying concentration to said absorbing/desorbing means; and
means, responsive to said electrode signal, for indicating the rate of change of said substrate temperature with time (dT/dt) where a change in the slope of dT/dt versus time is an indication of the presence of said fluid.

16. The pyroelectric sensor of claim 15, wherein said applying means varies said concentration between a low and a high concentration of said fluid in said test medium and said temperature changing means includes means for varying the temperature of said absorbing- /desorbing means through a temperature at which said absorbing/desorbing means desorbs said fluid at a low concentration in said test medium and absorbs said fluid at said high concentration in said test medium.

17. A pyroelectric fluid sensor for determining at least the presence of a fluid in a test medium, said sensor comprising:

a pyroelectric substrate having at least first and second portions;

first electrode means for deriving a first signal from said first portion of said pyroelectric substrate when the temperature of said first portion changes;

second electrode means for deriving a second signal from said second portion of said pyroelectric substrate when the temperature of said second portion changes;

means for changing the temperature of said pyroelectric substrate;

temperature dependent means for absorbing and for desorbing said fluid, said absorbing/desorbing means in substantial thermal contact with only said first portion of said pyroelectric substrate;

means for applying said fluid in said test medium in a periodically varying concentration to said absorbing/desorbing means; and means for comparing said first and second signals and for indicating the presence of said fluid when said first signal is substantially different from said second signal.

18. The pyroelectric fluid sensor according to one of claims 1, 3, 9, 15 or 17, wherein said temperature dependent means comprises a catalyst, said catalyst serving to promote a temperature varying reaction with said fluid in said test medium.

19. The pyroelectric sensor of claim 17, wherein said applying means varies said concentration between a low and a high concentration of said fluid in said test medium and said temperature changing means includes means for varying the temperature of said absorbing-/desorbing means through a temperature at which said absorbing/desorbing means desorbs said fluid at a low concentration in said test medium and absorbs said fluid at said high concentration in said test medium.

20. A pyroelectric fluid sensor according to one of claims 1, 3, 9, 15 or 17, wherein said temperature dependent means is one of an enzyme and coenzyme, where said one of an enzyme and coenzyme provides a temperature variation upon reacting with a respective one of a coenzyme and enzyme where said one of a coenzyme and enzyme comprise the fluid whose presence is to be detected.

* * * * *